United States Patent
Nikkonen et al.

(10) Patent No.: US 7,282,616 B2
(45) Date of Patent: Oct. 16, 2007

(54) PROCESS FOR CONVERSION OF OLEFINS

(75) Inventors: Jouko Nikkonen, Hamari (FI); Jyrki Hiltunen, Sipoo (FI); Jaana Makkonen, Söderkulla (FI); Marja Tiitta, Vantaa (FI); Isto Eilos, Porvoo (FI); Pasi Hagelberg, Espoo (FI)

(73) Assignee: Fortum Oyj, Espoo (FI)

( * ) Notice: Subject to any disclaimer, the term of this patent is extended or adjusted under 35 U.S.C. 154(b) by 262 days.

(21) Appl. No.: 10/450,949

(22) PCT Filed: Dec. 19, 2001

(86) PCT No.: PCT/FI01/01136
§ 371 (c)(1),
(2), (4) Date: Jul. 15, 2003

(87) PCT Pub. No.: WO02/49996
PCT Pub. Date: Jun. 27, 2002

(65) Prior Publication Data
US 2004/0049092 A1    Mar. 11, 2004

(30) Foreign Application Priority Data
Dec. 19, 2000   (FI) .................................. 20002783

(51) Int. Cl.
*C07C 2/54*   (2006.01)
*C07C 2/66*   (2006.01)

(52) U.S. Cl. ................... 585/446; 585/447; 585/571; 585/922

(58) Field of Classification Search ................ 585/446, 585/447, 671, 922
See application file for complete search history.

(56) References Cited

U.S. PATENT DOCUMENTS

| | | | |
|---|---|---|---|
| 5,198,590 A | 3/1993 | Sofranko et al. | |
| 5,336,820 A | 8/1994 | Owen et al. | |
| 5,789,640 A * | 8/1998 | Jin et al. | 585/467 |

FOREIGN PATENT DOCUMENTS

| | | |
|---|---|---|
| WO | WO97/45383 A1 | 12/1997 |
| WO | WO98/08599 A1 | 3/1998 |
| WO | WO98/08600 A1 | 3/1998 |

\* cited by examiner

*Primary Examiner*—Thuan Dinh Dang
(74) *Attorney, Agent, or Firm*—Birch, Stewart, Kolasch, and Birch, LLP (57) ABSTRACT

A process for converting an olefin feed to hydrocarbons suitable for fuel components or their feedstock. According to the process, an olefin feed, possibly together with another hydrocarbon feed, is contacted in a reactor with a catalyst in order to produce a hydrocarbon having at least one alkyl side chain. In the invention, the olefin feed is contacted with a particle-form fluidized catalyst in a circulating-bed reactor, wherein the catalyst forms the circulating bed of the reactor. When the operation is carried out in a circulating-bed reactor, the retention time of the feedstock is short. In this case, iso-olefins are formed quite selectively from n-olefins in isomerization. Since the useful life of the catalyst lengthens while the catalytic activity of the bed remains high for a long time, the conversion level also remains high. A long useful life of the catalyst is an economically highly significant advantage. In a circulating-bed reactor the regeneration of the catalyst can be carried out quite flexibly, and the operation of the reactor need not be interrupted for the duration of regeneration.

13 Claims, 3 Drawing Sheets

PROCESS FOR CONVERSION OF OLEFINS

This application is the national phase under 35 U.S.C. § 371 of PCT International Application No. PCT/FI01/01136 which has an International filing date of Dec. 19, 2001, which designated the United States of America.

The present invention relates to the process according to the preamble of Claim 1 for converting an olefin feed to gasoline components or to hydrocarbons suitable for use as feedstock for gasoline components.

According to a process such as this, the olefin feed, possibly together with another hydrocarbon feed, is contacted in a reactor with a catalyst in order to produce a hydrocarbon having at least one alkyl side chain.

Light n-olefins can be converted to more valuable gasoline components or to feedstock for gasoline components primarily by means of two processes, namely, isomerization and respectively alkylation. When n-olefins are isomerized, iso-olefins are obtained. Iso-olefins are reactive in, for example, etherification, dimerization and oxidation. In alkylation, light olefins are caused to react in the presence of a catalyst, at elevated temperature and pressure, with hydrocarbons such as cyclic, in particular aromatic, compounds, in order to prepare modified hydrocarbon products having at least one alkyl side chain. One example of alkylation is the alkylation of $C_6$-$C_8$ aromates with $C_3$-$C_4$ olefins, the product being $C_7$-$C_{11}$ alkyl aromates, since other reactions, for example cracking, also take place during the reaction. These can be mixed with gasoline fractions, and they are components considerably more valuable than the feedstock.

In general, isomerization reactions are carried out in solid-bed reactors at elevated temperatures (at approx. 200-500° C.). There is commercially available a butene isomerization process licensed by Lyondell and the ISOFIN process developed by Mobil and British Petroleum for the isomerization of butanes and pentanes. From the patent literature there are known numerous isomerization processes for an olefin feed. One example is the option according to U.S. Pat. No. 5,198,590.

Skeletal isomerism for n-olefins is obtained at the acid sites of catalysts. Typical catalysts in which skeletal isomerization reactions of n-olefins do occur include zeolites, other molecular sieves, such as SAPO-11, amorphous aluminum silicates and aluminum oxides. The most researched zeolites in the structural isomerism reaction are zeolites belonging to the theta-1 and ferrierite groups.

Aluminum silicate catalysts, in particular zeolites, are also used in alkylation.

There are certain drawbacks involved in the state-of-the-art technology. In particular it is to be noted that all of the catalysts mentioned above are deactivated relatively rapidly. According to the examples in GB-A-2-060 424, their useful lives may be as short as 1-2 h. It is often necessary to add steam and halogen compounds to extend the useful life of the catalyst. DE-3 000 650 states that the operating cycle can be increased to about 50 hours by these methods.

The alkylation reaction between olefins and isoparaffins is also known from, for example, WO application publication 97/45383. The performing of the reaction between olefins and aromatic hydrocarbons in a fluidized bed is disclosed in U.S. Pat. No. 5,336,820.

Of zeolite materials, typical catalysts suitable for the skeletal isomerization reaction are described in patent publications U.S. Pat. Nos. 4,503,282; 5,227,569; 4,435,311 and 4,392,003. Publications EP 0 523 838 and WO 95/17961 disclose a process for preparing a zeolite catalyst and isomerizing linear olefins to corresponding methyl-branched iso-olefins by using as catalysts zeolites having a pore size sufficiently small to slow down the formation of coke in the pore structure and sufficiently large to allow the reaction of the linear olefins to iso-olefins. With these improved catalysts, an operating cycle of 217 hours has been achieved (at least 33% by weight of isobutenes in the product). This ample week of useful life is, however, still rather short considering industrial processes in practice. In conventional processes the replacement of the catalyst causes production stoppages and increases costs.

At the beginning of the operating cycle, the fresh catalyst additionally has a period during which the iso-olefin selectivity is poor. This matter has been described in, for example, the 1993 Petrochemical Review publication "Highly Selective Olefin Skeletal Isomerization Process." An isobutene selectivity above 90% is typically not attained until after an operating time of 75 hours. The skeletal isomerization reaction of olefins has equilibrium limitations. Of pentenes, isopentenes can be present at a temperature of 200° C. in an amount of 89%, whereas at a temperature of 350° C. the amount of isopentenes can be only 81%. Respectively, at a temperature of 200° C., isohexenes can be in equilibrium in an amount of 95%, whereas at a temperature of 350° C. the amount of isohexenes in equilibrium can be 90%. When it is desired to maximize the yield of iso-olefins, it is preferable to carry out the reaction at as low a temperature as possible. In conventional processes (solid bed) the catalyst deactivation rate is higher the lower the temperature. Therefore the operating temperatures are often quite high when it is necessary to maximize the operating cycle.

The object of the present invention is to provide a completely novel process for converting an olefin feed to a more valuable gasoline component. It is a particular object of the invention to provide a process for the isomerization of n-olefins to corresponding iso-olefins or respectively the alkylation of an aromatic hydrocarbon feed with an olefin feed.

According to the invention, the conversion of an olefin feed is carried out in a circulating-bed reactor system, wherein the olefin feed is contacted with catalyst particles in a fluidized state. Circulating-bed reactor technology has previously been used in the chemical process industry, for example, for the preparation of a maleic acid anhydride and for the cracking of hydrocarbons. It is characteristic of circulating-bed reactors that the reaction bed flows through the reactor and that a portion, in general all, of it is directed continuously to regeneration. In the present invention it has been observed that a circulating-bed reactor system which includes a reactor, possibly with internal circulation, and a regenerator—equally with an internal circulation—provides a possibility for continuous regeneration of the catalyst, in which case the olefin feed conversion reaction can be carried out at a quite high and quite steady catalyst activity level for even long periods of time.

More precisely, the process according to the invention is mainly characterized in what is stated in the characterizing part of Claim 1.

Considerable advantages are gained through the invention. Thus, when the operation takes place in a circulating-bed reactor, the retention time of the feedstock is short. In this case, during isomerization, iso-olefins are formed from n-olefins quite selectively. Since the useful life of the catalyst is lengthened while the catalytic activity of the bed remains high for a long time, the conversion level also remains high. Owing to the high activity level, the reaction temperature can be lowered, which promotes the selective conversion of the olefins, in which case the formation of secondary products remains low. In U.S. Pat. No. 5,198,590 the temperature is 400-800° C., preferably 500-650° C. In the present invention the temperature is preferably below 400° C. Likewise, the retention time is longer in the prior-known process.

Similar advantages are gained in alkylation. A long useful life of the catalyst is financially a very significant advantage. In a circulating-bed reactor the regeneration of the catalyst can be managed quite flexibly, and the operation of the reactor need not be interrupted for the duration of the regeneration. This reduces apparatus expenses, since it is not necessary to incorporate into the apparatus two parallel reactor units of which one has to be kept in reserve. An operating cycle for the regeneration is not necessary, and therefore it is not necessary to have several reactors.

In the process according to the invention, the coke formed in the catalyst is easy to remove, since the reaction temperature is lower and the retention time is shorter than when a solid-bed reactor is used.

In a preferred embodiment of the invention, an annular-structured reactor is used. Thereby considerable advantages are gained in the present processes. Thus, the retention times are quite short (at maximum 3 s, typically 0.1-2.5 s). Clearly longer retention times are mentioned in the above-mentioned patent publications concerning alkylation processes. Short retention times can be used owing to the use of advantageous flow regions (turbulent/rapid fluidization), which enables conditions advantageous for the reaction to be achieved with a low gas flow velocity in the reactor (back flow of the gas is minimized), and the transfer of material is maximized. Owing to the low flow velocities, erosion of the structures and attrition of the particles are considerably less than in normal circulating-bed reactors wherein the flow velocities are 5 . . . 10-fold. Depending on the catalyst, the velocity is 0.1-3 m/s, preferably 0.2-2 m/s, and in particular approx. 0.5-1.5 m/s.

Owing to the annular-structured reactor it is possible to use for separation a multi-inlet cyclone technology, which makes a good separation capacity possible at low cyclone inlet flows but, nevertheless, a rapid separation of gas and particles from each other. In a preferred embodiment of the present invention, the apparatus therefore has preferably a separation device made up of a multi-inlet cyclone or a cascade of several multi-inlet cyclones. Such a separation device is especially suitable for processes in which the retention time is short and the C/O ratio is high.

Other advantages gained through the process include:

the reactor size is small, since it is a short retention time reactor the amount of catalyst in the reactor is smaller than in a solid-bed reactor, and the reactor contains a smaller amount of hydrocarbons per time unit, which is a safety advantage.

The invention will be described below in greater detail with the help of the accompanying drawings.

According to a first preferred embodiment, our invention is based on the use of a continuous-working fluidized-bed reactor in the preparation of iso-olefins from n-olefins. The temperature is typically 25-400° C., most suitably below 400° C.

An especially suitable method is to use the circulating-bed reactor described in patent publication FI 101 156 B. By this process it is possible to prepare iso-olefins continuously and with high selectivity (over 80%). By this process it is possible to maintain the amount of coke at a suitable level so that there is no non-selective period at the beginning of the operating cycle or after regeneration. By this process, iso-olefins can be prepared at a lower temperature than in a conventional solid-bed reactor, since, owing to the short retention time, there occur fewer secondary reactions causing deactivation and the activity of the catalyst can be maintained high by the use of suitable reaction and regeneration times. The temperature used in the regeneration may also be lower than conventional, since the coke forming during the reaction is easy to remove.

In another embodiment of the invention, a circulating-bed reactor is used for the alkylation of aromates. The alkylation is usually carried out at 170-500° C.

In the process according to the invention, the isomerization reaction and regeneration are carried out continuously.

In the present invention, by "retention time" is meant the average retention time of hydrocarbon from the feeding point to the outlet pipe of the solids separation means, i.e. in practice the cyclone, of the circulating-bed reactor, which time may be 0.05-10 seconds, but is typically 0.1-5 s.

By "solids" is meant the material which, together with gas, forms a suspension in the reaction chamber. The solids are made up of solid catalyst particles. The catalyst is selected according to the process. Thus, natural or synthetic aluminum silicates, zeolites and alumina are primarily used for isomerization. The conventional zeolites catalyzing isomerization include ferrierites and theta-1 type zeolites. For alkylation, for example a ZSM-5 type zeolite is used.

The reactor system used for implementing the invention may comprise two separate reactor units, of which one is used as a reactor and the other as a regenerator. Typically, in the reactor the hydrocarbon product and the catalyst are separated in a cyclone apparatus, at least a portion of the catalyst particles of the circulating-bed reactor are directed to the regeneration unit, where the catalyst particles are regenerated at an elevated temperature, and the regenerated catalyst particles are recycled to the circulating-bed reactor. Preferably a circulating-bed reactor is used as the regeneration unit. The cyclone apparatus is normally made up of two cyclones in series, at least the latter of them in the gas flow direction being preferably a multi-inlet cyclone.

According to a preferred embodiment of the invention, the reactor and/or regenerator has an internal circulation, which has been implemented by connecting the dipleg of the separation means, usually a multi-inlet cyclone, to the feed port for the fluidization gas or respectively regeneration air, or preferably to a point above the feed port, in the lower part of the riser.

Compared with the above-mentioned patent publications, one important difference between the invention and the state of the art is the absence of the internal catalyst circulation in such a reactor. The advantages described in the present invention cannot be achieved with a once-through reactor. As stated above, a slightly used catalyst provides a higher selectivity than does a regenerated catalyst. Thus, in the present invention the catalyst circulates through the riser and the cyclone at least 5, preferably at least 10 times, for example, approx. 15-150 times, in particular approx. 17-30 times, before ending up on the regenerator side. From the solids/catalyst amount flowing in the dipleg respectively at least approx. 0.5%, preferably approx. 1-20%, typically approx. 5-15% is in this case circulated via a return pipe to the reactor.

The regenerator preferably has corresponding internal circulation, in which case—as above—the catalyst circulates via the riser and the cyclone at least 5, preferably at least 10 times, for example approx. 15-150 times, in particular approx. 17-30 times, before ending up in the reactor riser. Even in this case at least approx. 0.5%, preferably approx. 1-20%, typically approx. 5-15%, of the solids/catalyst amount flowing in the dipleg is in circulated via a return pipe to the regenerator.

Between the regenerator and the reactor there prevails a large temperature difference, and the energy requirement of the reaction is small. If internal circulation is not used, either the catalyst needs to be cooled before being directed to the reactor (a large amount of energy for cooling) or a low C/O ratio needs to be used, which leads to a decrease in conversion.

A reactor unit used as a circulating-bed reactor comprises, for example,
- a tubular or annular riser having a substantially vertical central axis,
- a cyclone apparatus arranged at the upper end of the riser as an extension of the riser, the cyclone having one or several inlet ports connected to the riser and, an outlet port, and
- a dipleg connected to the lower outlet port of the cyclone apparatus, the dipleg being arranged substantially concentrically inside the riser or non-concentrically next to the riser and having a substantially annular or circular cross section in the transverse direction.

The regeneration unit used is an apparatus comprising
- a tubular or annular riser having a substantially vertical central axis,
- a multi-inlet cyclone arranged at the upper end of the riser as an extension of the riser, the cyclone having one or several inlet ports connected to the riser, and an outlet port, and
- a dipleg connected to the lower outlet port of the cyclone, the dipleg being arranged substantially concentrically inside the riser or non-concentrically next to the riser and having a substantially annular or circular cross section in the transverse direction.

Figure 1:
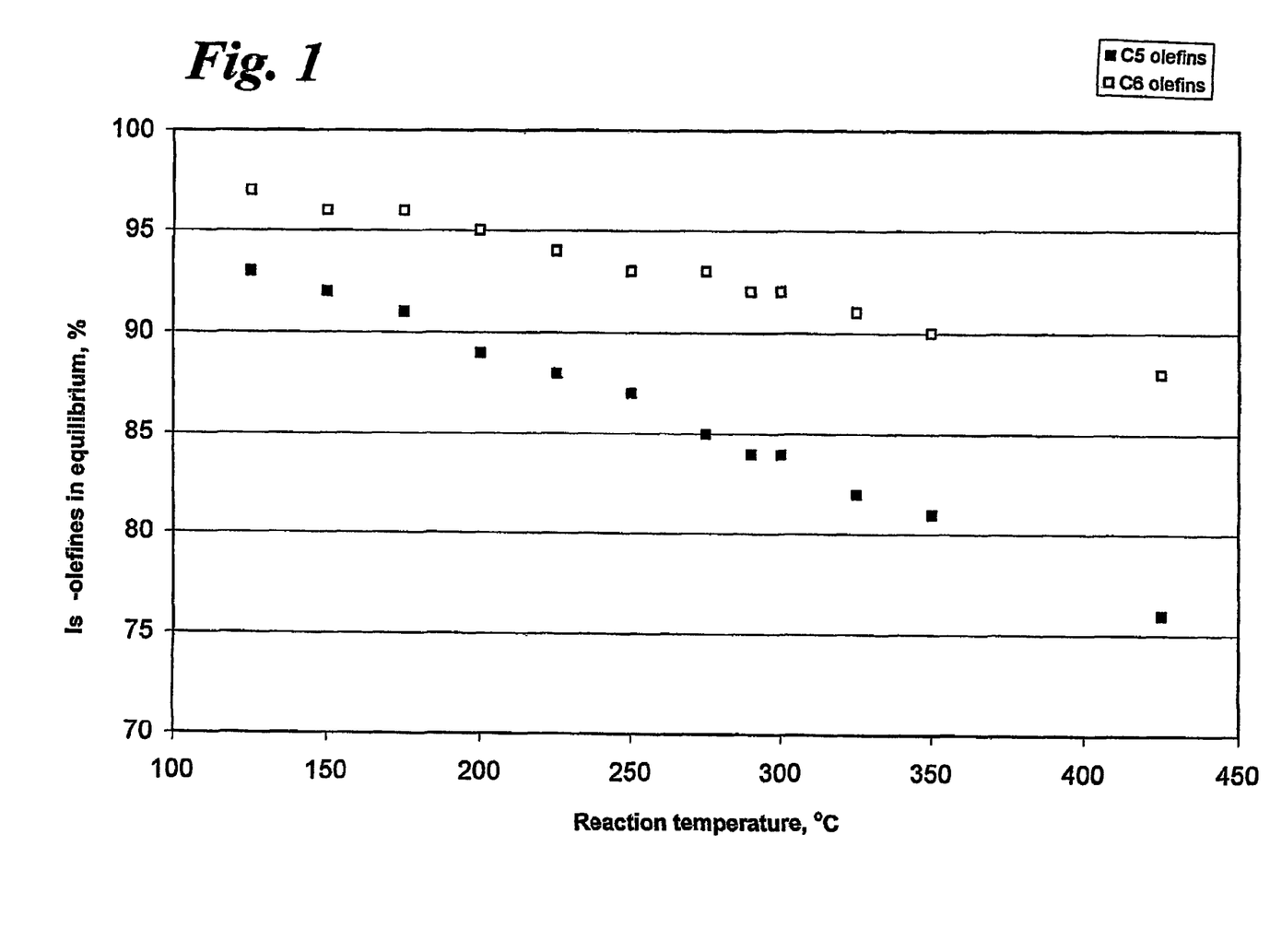
FIG. 1 shows how, when an equilibrium catalyst is in use, the yields of olefins in skeletal olefin isomerization are improved when the reactor temperature is lowered.
Figure 2:
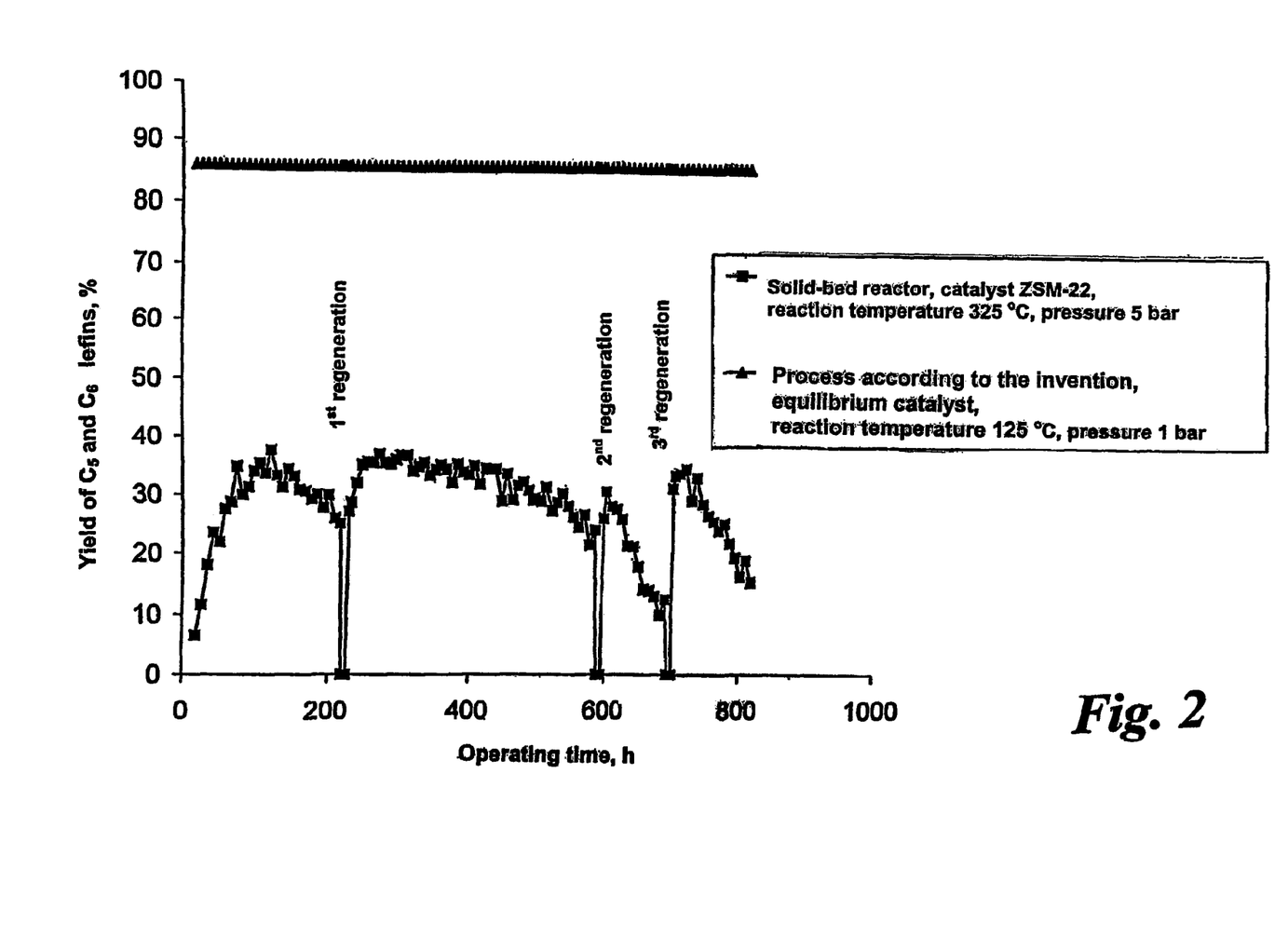
FIG. 2 depicts the iso-olefin yield in olefin isomerization by a conventional process with a solid-bed reactor and by the process according to the invention.
Figure 3:
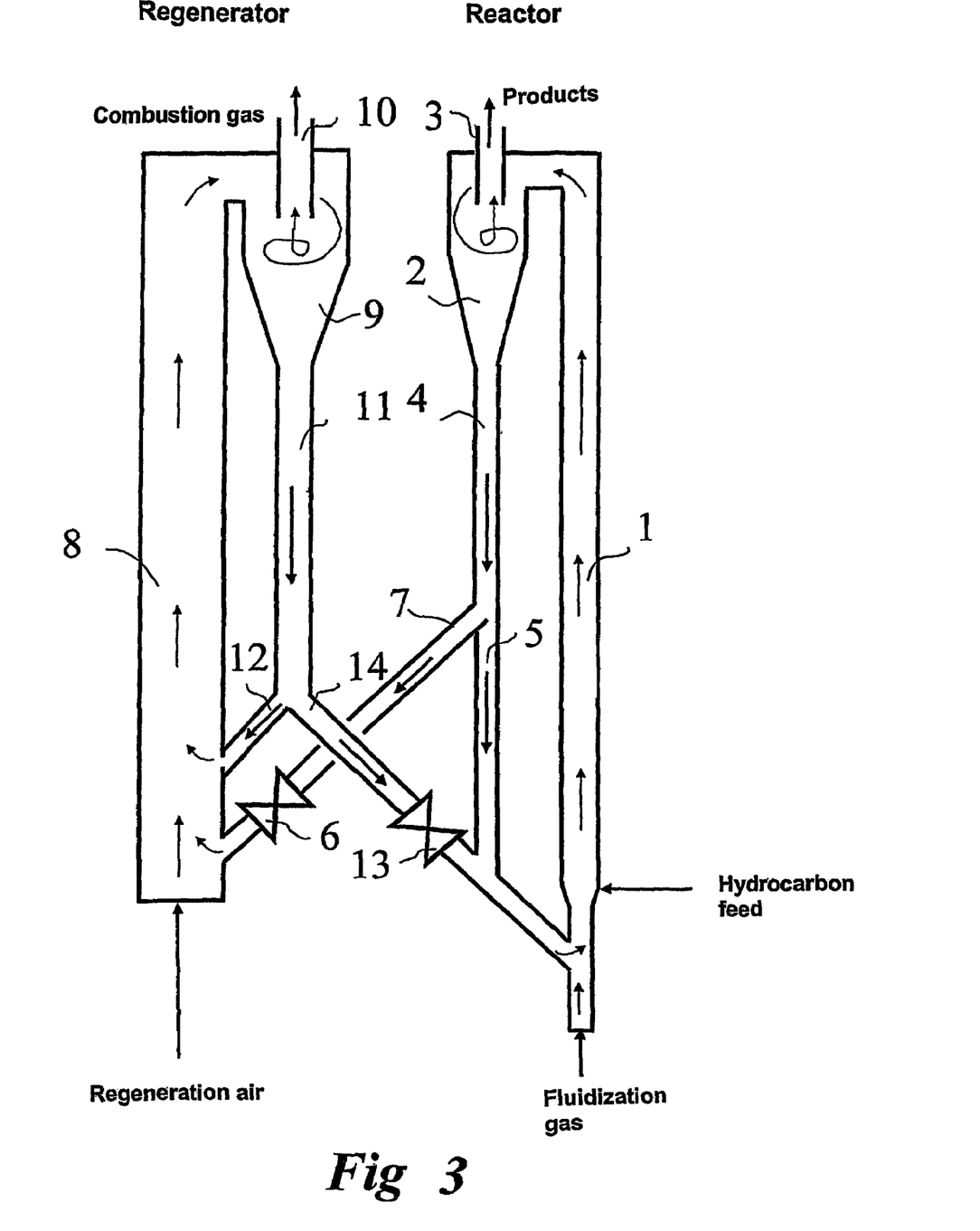
FIG. 3 depicts, as a representation of the principle, the structure of the reactor/regenerator unit used in the process according to the invention.

FIG. 3 depicts the principle of the coupling of two circulating-fluid-bed reactors:

The hydrocarbon is fed into the lower portion of the reactor. If it is desired to feed the hydrocarbon into a dilute suspension, a pre-fluidization gas (e.g. nitrogen) is fed separately into the lower portion of the reactor. The gaseous-state hydrocarbon transports the catalyst in the riser 1 of the reactor, the hydrocarbon reacting to form the desired compounds. The hydrocarbon-catalyst suspension further travels to the cyclone 2, where the hydrocarbon is separated from the catalyst. The hydrocarbon leaves via an outlet port 3 to the product processing part, and the spent catalyst travels through the cyclone leg 4 into the reactor return conduit 5 and from there again to the reactor riser 1. A portion of the spent catalyst is regulated by means of a valve 6 to travel through a transfer pipe 7 into the regeneration part, where the catalyst is fluidized by means of regeneration air introduced into the lower portion of the regenerator. The catalyst travels together with the combustion air through the regenerator riser 8, whereupon the coke on the catalyst surface is oxidized and the catalyst temperature rises. The suspension of combustion gas and catalyst travels to the cyclone 9, where the combustion gas is separated from the catalyst. The combustion gas is removed via an outlet port 10, for example to the heat recovery unit, the catalyst traveling through the cyclone leg 11 to the regenerator return conduit 12, and from it again to the regenerator riser 8. A regenerated catalyst amount corresponding to the spent catalyst coming from the reactor to the regenerator is regulated by means of a valve 13 to travel through a conduit 14 to the reactor.

The above description does not apply only to an apparatus made up of a separate reactor and a separate regenerator; it is also possible to use an "onion"-structured apparatus according to patent FI 101156, wherein the reactor and regenerator parts are fitted one inside the other. The first-mentioned is advantageous in alkylation, either alternative is advantageous in isomerization. In an onion-structured circulating-bed reactor the reaction chamber is between two vertical cylinders or cones one inside the other, in which case the reaction chamber and the solids dipleg are annular in cross-section. The feed nozzles via which the liquid, or in some cases gaseous, feed is directed to the reaction chamber are in the lower portion of the reaction chamber. They are normally oriented upwards. The catalyst is directed from the dipleg of the reactor to the lower portion of the reactor via an annular inlet in the lower portion of its outer mantle or via smaller inlets in the mantle. The solids flow into the reactor is preferably regulated by closing means of the said inlets; by turning or lifting the closing means the solids inlet can be throttled. Conventional valves can also be used for regulating the solids flow from the dipleg to the reactor.

For the regeneration of the catalyst the reaction chamber is connected to the regeneration unit via a dipleg at a point after the cyclone. In the case of an onion-structured reactor, one reactor can be disposed inside another reactor. Of these two reactors it is often advantageous to use the inner one as the cracking reactor and the outer one as the regenerator wherein the recyclable catalyst is regenerated and heated to the desired temperature. The catalyst is transferred from the reactor to the regenerator in the onion structure via a conduit, i.e. a dipleg, having an annular cross-section and via conduits passing through the fluidization chamber of the reactor. The regenerator dipleg, i.e. the catalyst return conduit to the reactor, is also a chamber annular in cross-section. As to the state of the art, reference is made to the apparatuses according to EP patent publications 0 863 796 and 0 888 174.

In the onion structure, most preferably a multi-inlet cyclone serves as the means, attached to the upper portion of the reaction chamber, for separating solids from the reaction product. In such a cyclone the solids suspension to be treated is fed into the cyclone chamber through a plurality of inlets. The inlets may be symmetrically or asymmetrically arranged relative to the vertical axis. Preferably the inlets are arranged symmetrically, since the riser has an annular cross-section and the flow is thus uniform over the entire cross-section of the riser. In a case such as this the cyclone is equipped with flow guide vanes by means of which the vortex required by centrifugal separation is produced. The guide vanes are typically arranged annularly as a guide vane system on the circumference of the cyclone chamber in such a manner that this system forms a plurality of parallel gas inflow conduits. If the catalyst particle size used is small, as in general, it is advisable to use two concentrically disposed multi-inlet cyclones in series in the gas flow direction.

In another preferred embodiment of the invention, $C_6$-$C_8$ aromates are alkylated with olefins to alkyl aromates in a circulating-bed reactor. In the method the aromates are alkylated with light olefins with the help of a zeolite catalyst. The feed ratio of the $C_6$-$C_8$ aromates and $C_2$-$C_4$ olefins, used as the feed, is typically approx. 5-20:1 at a temperature of 150-500° C. and a pressure of 110-5000 kPa(g).

In alkylation both the actual reaction and the regeneration are exothermal processes. This means that the reactor system has to be cooled. Furthermore, the reaction occurs under a pressure higher than that of the FCC process, which means that when the process is implemented with the option according to the reactor concept, also regeneration has to be carried out as pressurized combustion. For this reason, alkylation is preferably carried out in a reactor system wherein the reaction and the regeneration are carried out in separate pressure vessels. In this case the cooling for the reactor system is easy to arrange, as is also the focusing of the feeds at different heights in the reactor riser. A high pressure favors the separate-reactor option in terms of investment costs, since the price of the pressure mantle is significantly affected by its diameter, which is in an "onion structure" significantly greater than in the separate-reactor option.

In alkylation, for example the apparatus according to EP patent 0 753 037 (FI patent application 941528) or FIG. 3 can be used. By using this option it is possible to reduce the effect of the wall on the flow profile. When CFB reactors are applied to reactions which do not require or yield much heat and which produce less coke, deactivation is slower. In this case it is advantageous to use a reactor having a so-called internal cycle, i.e. the catalyst on average circulates in the reaction zone several times before it ends up in regeneration.

The feed of the process according to the invention generally comprises an olefin-containing hydrocarbon composition. The feed typically contains at least 10% by weight, preferably 20% by weight, of olefins serving as the feedstock material. The olefins are, for example, linear 1- or 2-butene, isobutene, and linear or branched $C_5$ olefins. Alternatively the feed may comprise a mixture of these olefins. The feed contains most preferably $C_4$ olefins, advantageously n-butene, from which isobutene is obtained by isomerization, and/or $C_5$ olefins, from which isopentene is obtained by isomerization. It is clear that the feed may contain both $C_4$ and $C_5$ olefins, in which case the product obtained is a mixture of isobutene and isopentenes.

When the process according to the invention is used for alkylation, the hydrocarbon feed also contains aromatic compounds, preferably compounds containing 6-8 carbon atoms, in particular benzene, in which case alkylation produces $C_{7-11}$ alkyl aromatic hydrocarbons, such as toluene, xylene, ethyl benzene, methylethyl benzene, diethyl benzene, propyl benzene and methylpropyl benzene. The aromatic fraction may comprise, for example, reformed gasoline.

According to the first preferred embodiment, in which a $C_4$-based hydrocarbon fraction is isomerized, the hydrocarbon mixture of the feed comprises n-butene at least 10% by weight, preferably at least approx. 20% by weight. The feed may be made up of pure n-butene, but in practice the $C_4$-based hydrocarbon fraction from oil refining is used for the feed. Preferably the $C_4$ fraction obtained from FCC, TCC, DCC or RCC is used, or a $C_4$ fraction obtained from the ethylene unit after the removal of butadiene (Raffinate 1). Of the above, the FCC, RCC, TCC and Raffinate 1 fractions are especially advantageous, since the said hydrocarbon fraction can be used as such, possibly after the separation of the heavy ($C_{8+}$) fractions. Raffinate 1 typically comprises approximately 50% by weight of isobutene, approx. 25% by weight of linear butenes, and approx. 25% by weight paraffins. The FCC product typically comprises 10-50, advantageously approx. 10-30% by weight of isobutene, 20-70% by weight of 1- and 2-butene, and approx. 5-40% by weight of butane. An example of a typical FCC mixture is one having the composition: approx. 30% by weight of isobutene, approx. 17% by weight of 1-butene, approx. 33% by weight of 2-butene, and approx. 20% by weight of butane.

1- and 2-butene prepared from chemicals may also be used.

If the invention is used for the alkylation of aromates to prepare corresponding alkyl aromates, the olefin feed used is most preferably an FCC combustion gas stream which contains $C_{1-4}$ hydrocarbons, such as ethylene, propylene and butene. Typically such a gas stream contains approx. 10-20% by weight of ethylene, 15-40% by weight of propylene and 20-40% by weight of butenes, as well as a small amount of methane and paraffinic hydrocarbons.

According to another embodiment of the invention, the feed comprises the $C_5$ fraction of FCC gasoline, of light FCC gasoline, of pyrolysis-$C_5$ gasoline, of TCC gasoline, of RCC gasoline or of Coker gasoline, typically of FCC gasoline, and it may thus also comprise $C_6$ olefins. Preferably the FCC fraction is fractionated in order to obtain as pure a $C_5$ olefin fraction as possible, in which the concentration of other $C_5$ hydrocarbons is lower than 15% by weight, preferably lower than 5% by weight. It is also possible to use a fraction which also comprises $C_6$ olefins. Typically the feed thus comprises 20-60% by weight, in particular 30-50% by weight, of $C_5$ olefins; 10-30% by weight, in particular 15-25% by weight, of $C_6$ olefins; and 15% by weight or less of paraffinic hydrocarbons.

According to a third embodiment, the feed comprises both $C_4$ and $C_5$ olefins. In this case the hydrocarbon feed selected is a FCC, TCC, DCC or RCC fraction or Raffinate 1, FCC gasoline, light FCC gasoline, pyrolysis-$C_5$ gasoline, TCC gasoline, RCC gasoline or Coker gasoline. An easily available hydrocarbon composition comprises the $C_4$ and $C_5$ fractions of FCC. Preferably the composition contains at least 10% by weight, in particular at least 15% by weight, of $C_4$ olefins and at least 10% by weight, in particular at least 15% by weight, of $C_5$ olefins. Typically the amounts of $C_4$ olefins and $C_5$ olefins are approximately equal, although usually the fraction contains a slightly larger amount of $C_4$ olefins.

EXAMPLES

The following examples show that iso-olefins are selectively formed from n-olefins when the retention time in the reaction is short. In all of the experiments, a 97% by weight pure 1-pentene was used according to Fluka. The equipment in the experiments was a pulse reactor that is described in detail in the Applied Catalysis journal article General 183 (1999) 411-421 (Novel equipment for testing catalytic cracking and catalyst regeneration with short contact times, K. Lipiäinen et al.). The catalyst particle size used in the experiments was 0.074-0.149 mm. The retention time was calculated as follows:

$$\text{Retention time}(s) = \frac{\text{catalyst layer volume (µl)}}{\text{carrier gas flow velocity (µl/s)}} \quad (1)$$

The results determined from the gas chromatographic analyses were calculated from the following formulae, where S=in the feed and T=in the products $$\text{conversion of } n\text{-pentenes} = \frac{(1 - C_5^= S - (1 - C_5^= + t\text{-}C_5^= + c\text{-}2\text{-}C_5^=)T \times 100 \text{ wt. \%}}{(1 - C_5^= S)} \quad (2)$$

$$\text{iso-olefin selectivity} = \frac{((3\text{-me-}1\text{-}C_4^= + 2\text{-me-}1\text{-}C_4^= + 2\text{-me-}2C_4^=)T) \times 100 \text{ wt. \%}}{(\text{conversion of } n\text{-}C_5^=)} \quad (3)$$

$$\text{isopentene yield} = \frac{(\text{conversion of } n\text{-}C_5^= \times \text{iso-olefin selectivity wt. \%})}{100} \quad (4)$$

$$\text{isopentenes (\%) of the thermodynamic equilibrium} = \frac{(3\text{-me-}1\text{-}C_4^= + 2\text{-me-}1\text{-}C_4^= + 2\text{-me-}2C_4^= \text{ thermodyn proportion of iso-olef.} \times 100 \text{ wt. \%}}{(1\text{-}C_5^= + t\text{-}2\text{-}C_5^= + c\text{-}2\text{-}C_5^= + 3\text{-me-}1\text{-}C_4^= + 2\text{-me-}1\text{-}C_4^= + 2\text{-me-}2\text{-}C_4^=)} \quad (5)$$

Examples 1-25 show the behavior of 1-pentene with a short retention time when the catalyst is commercial ferrierite HSZ-720-KOA. Before the testing, the ferrierite was ion-exchanged with a 3 M ammonium nitrate solution. During this treatment the potassium and sodium ions present in the zeolite were removed. Thereafter the zeolite was calcined at 500° C. for two hours, whereby the ammonium ions broke down to ammonia and acid sites.

TABLE 1

| Example | Retention time, ms | Temperature, ° C. | n-pentene/catalyst, mmol/g | Conversion, wt. % | Isopentene selectivity, wt. % | Isopentene yield, wt. % | Isopentenes (%) of equilibrium |
|---|---|---|---|---|---|---|---|
| 1 | 2 | 125 | 1.3 | 35 | 100 | 35 | 38 |
| 2 | 2 | 125 | 2.6 | 35 | 100 | 35 | 38 |
| 3 | 2 | 125 | 5.1 | 27 | 100 | 27 | 28 |
| 4 | 2 | 125 | 6.4 | 11 | 100 | 11 | 12 |
| 5 | 2 | 225 | 1.3 | 84 | 83 | 69 | 92 |
| 6 | 2 | 225 | 2.6 | 78 | 83 | 66 | 86 |
| 7 | 2 | 225 | 3.9 | 71 | 84 | 60 | 76 |
| 8 | 2 | 225 | 6.4 | 57 | 83 | 47 | 60 |
| 9 | 2 | 225 | 9.0 | 53 | 85 | 45 | 56 |
| 10 | 2 | 325 | 1.3 | 87 | 55 | 48 | 96 |

TABLE 1-continued

| Example | Retention time, ms | Temperature, °C. | n-pentene/catalyst, mmol/g | Conversion, wt. % | Isopentene selectivity, wt. % | Isopentene yield, wt. % | Isopentenes (%) of equilibrium |
|---|---|---|---|---|---|---|---|
| 11 | 2 | 325 | 2.6 | 87 | 59 | 51 | 96 |
| 12 | 2 | 325 | 3.9 | 86 | 61 | 53 | 97 |
| 13 | 2 | 325 | 5.1 | 86 | 61 | 53 | 97 |
| 14 | 2 | 325 | 6.4 | 86 | 61 | 53 | 97 |
| 15 | 3 | 325 | 2.6 | 84 | 67 | 57 | 96 |
| 16 | 3 | 325 | 5.1 | 84 | 68 | 57 | 96 |
| 17 | 3 | 325 | 7.7 | 84 | 70 | 59 | 96 |
| 18 | 3 | 325 | 10 | 84 | 70 | 59 | 95 |
| 19 | 5 | 325 | 3.9 | 84 | 72 | 60 | 96 |
| 20 | 5 | 325 | 7.7 | 83 | 73 | 60 | 96 |
| 21 | 5 | 325 | 9.0 | 83 | 72 | 60 | 96 |
| 22 | 5 | 325 | 12 | 83 | 74 | 61 | 96 |
| 23 (repeat) | 5 | 325 | 3.9 | 85 | 65 | 54 | 96 |
| 24 (repeat) | 5 | 325 | 7.7 | 85 | 66 | 55 | 96 |
| 25 | 5 | 325 | 12 | 84 | 68 | 57 | 96 |

The results of Examples 1-25 show that n-pentenes are converted to isopentenes with a high selectivity and a high conversion rate even though the retention time of the reaction is short. By the process according to the invention, the conversion of n-pentenes to isopentenes can be achieved even at a temperature of 125° C.

Examples 26-28 show the behavior of 1-pentene with a short retention time when the catalyst is commercial ferrierite HSZ-720-KOA which contains coke formed during the skeletal isomerization reaction.

TABLE 2

| Example | Retention time, ms | Temperature, °C. | n-pentene/catalyst mmol/g | Conversion, wt. % | Isopentene selectivity, wt. % | Isopentene yield, wt. % | Isopentenes (%) of equilibrium |
|---|---|---|---|---|---|---|---|
| 26 | 2 | 325 | 1.3 | 72 | 100 | 72 | 88 |
| 27 | 2 | 325 | 2.6 | 65 | 100 | 65 | 80 |
| 28 | 2 | 325 | 3.9 | 60 | 100 | 60 | 74 |

A comparison of the results of Examples 26-28 (carried out with coked catalyst) with the results of Examples 10-12 (carried out with fresh catalyst) shows that the behavior of the at a suitable coke level increases the iso-olefin yield.

Examples 29-34 show the behavior of 1-pentene with a short retention time when the catalyst is zeolite ZSM-22 belonging to the theta-1 group. The purpose of the examples is to show that the process according to the invention can be applied to various catalysts.

TABLE 3

| Example | Retention time, ms | Temperature, °C. | n-pentene/catalyst mmol/g | Conversion, wt. % | Isopentene selectivity, wt. % | Isopentene yield, wt. % | Isopentenes (%) of equllibrium |
|---|---|---|---|---|---|---|---|
| 29 | 150 | 125 | 1.3 | 28 | 67 | 19 | 23 |
| 30 | 150 | 125 | 2.6 | 21 | 42 | 9 | 11 |
| 31 | 150 | 225 | 1.3 | 81 | 73 | 59 | 86 |
| 32 | 150 | 225 | 2.6 | 79 | 74 | 58 | 83 |
| 33 | 150 | 325 | 1.3 | 87 | 51 | 44 | 95 |
| 34 | 150 | 325 | 2.6 | 87 | 52 | 45 | 95 |

The invention claimed is:

1. A process for converting an olefin feed to hydrocarbons suitable for fuel components or their feedstock, which process comprises:

contacting the olefin feed, optionally together with another hydrocarbon feed, in a reactor with a catalyst in order to produce a hydrocarbon having at least one alkyl side chain, wherein the olefin feed is contacted with a fluidized catalyst in particle form in a reactor with a circulating bed, such that the contact time between the olefin feed and the catalyst is 0.0001-5 seconds and the retention time of the feed in the reactor is 0.01-3 seconds, said reactor comprising a reactor unit having a tubular or annular riser having a substantially vertical central axis, a cyclone apparatus for separating gaseous hydrocarbon from solids which includes at least one multi-inlet cyclone, and which is arranged at the upper end of the riser as a continuation or the riser, and in which the cyclone has one or several inlet ports connected to the riser and separate outlet ports for the solids and the gas, and a dipleg connected to the solids outlet port of the cyclone, which dipleg is arranged substantially concentrically around the riser and has in the transverse direction a substantially annular or tubular cross-section; and wherein the catalyst constitutes the circulating bed in the reactor and the catalyst circulates through the riser and the cyclone at least ten times before being directed to a regeneration unit;

the hydrocarbon product and the catalyst are separated in a cyclone;

the catalyst particles directed to a regeneration unit are regenerated at an elevated temperature; and the regenerated catalyst particles are recycled to the circulating-bed reactor.

2. The process according to claim 1, wherein the regeneration unit used is a circulating-bed reactor.

3. The process according to claim 1, wherein the riser has a tubular or annular shape.

4. The process according to any of claims 1 or 2 or 3, wherein the regeneration unit used is an apparatus comprising a tubular or annular riser having a substantially vertical central axis, a cyclone apparatus which includes at least one multi-inlet cyclone, and which is arranged at the upper end of the riser as a continuation of the riser, and in which the cyclone has one or several inlet ports connected to the riser and an outlet port, and a dipleg connected to the gas outlet port of the cyclone, which dipleg is arranged substantially concentrically around the riser and has in the transverse direction a substantially annular or tubular cross-section.

5. The process according to claim 1, wherein iso-olefins are prepared from n-olefins.

6. The process according to claim 5, wherein the iso-olefin conversion from n-olefins reaction is carried out in the presence of a zeolite, SAPO, amorphous aluminum silicate or aluminum oxide catalyst.

7. The process according to claim 5 or 6, wherein the iso-olefin conversion from n-olefins reaction is carried out at a temperature of 25-400° C.

8. The process according to claim 5, wherein C4-7 iso-olefins are prepared.

9. The process according to claim 1, wherein the lower olefin is fed into the circulating-bed reactor together with an aromatic C6-C10 compound in order to prepare a C7-C11 alkyl aromate compound.

10. The process according to claim 9, wherein the alkylation of the aromatic compound is carried out at 170-500° C.

11. The process according to claim 1, wherein the contact time between the olefin feed and the catalyst is 0.001-1s.

12. The process according to claim 5, wherein isobutene or isoamylene is prepared.

13. The process according to claim 1, wherein the catalyst circulates through the riser and the cyclone approximately 15 to 150 times before being directed to a regeneration unit.

* * * * *